United States Patent [19]

Hill et al.

[11] Patent Number: 5,406,006
[45] Date of Patent: Apr. 11, 1995

[54] METHOD FOR PREPARING A PREFORMER CATALYST VIA IN-SITU ACTIVATION

[75] Inventors: Ronald R. Hill; Patricia B. Roussel, both of Baton Rouge, La.

[73] Assignee: Exxon Chemical Patents Inc, Linden, N.J.

[21] Appl. No.: 247,957

[22] Filed: May 24, 1994

[51] Int. Cl.$^6$ .................. C07C 45/49; C07C 45/50
[52] U.S. Cl. .................. 568/882; 568/451; 568/454; 568/492; 568/854; 568/909; 568/913; 502/25
[58] Field of Search ............ 252/413; 568/451, 492, 568/854, 882, 913, 909, 454

[56] References Cited

U.S. PATENT DOCUMENTS

| | | | |
|---|---|---|---|
| 3,725,534 | 4/1973 | Reisch | 423/417 |
| 3,855,396 | 12/1974 | Kniese et al. | 423/417 |
| 4,255,279 | 3/1981 | Spohn et al. | 252/413 |
| 4,400,299 | 8/1983 | Lagace et al. | 252/413 |
| 4,404,119 | 9/1983 | Lagace et al. | 252/413 |
| 4,447,661 | 5/1994 | Hoshiyama et al. | 568/882 |
| 4,625,067 | 11/1986 | Hanin | 568/451 |
| 5,237,104 | 8/1993 | Summerlin | 568/451 |
| 5,237,105 | 8/1993 | Summerlin | 568/451 |
| 5,321,168 | 6/1994 | Roussel et al. | 568/882 |

OTHER PUBLICATIONS

U.S. Ser. No. 08/122,859 filed Sep. 16, 1993 to Roussel et al.
U.S. Ser. No. 08/217,298 filed Mar. 23, 1994 to Hill, Jr. et al., Class 568, Subclass 451.

*Primary Examiner*—Werren B. Lone
*Attorney, Agent, or Firm*—John J. Mahon

[57] ABSTRACT

Carbonaceous preformer catalysts used to convert cobalt salts to hydrido cobalt carbonyl for use in the oxonation of olefins are activated or regenerated by treatment with an aqueous cobalt salt solution in the presence of a light alcohol having from about 4 to 7 carbon atoms and syn gas prior to exposure to or processing with any other organic stream at a temperature of about 120° C. to 190° C. and a pressure of about 13 MPa to 32 MPa for about 2 to 50 hours.

9 Claims, 4 Drawing Sheets

METHOD FOR PREPARING A PREFORMER CATALYST VIA IN-SITU ACTIVATION

This invention generally relates to an oxo process for preparing oxo alcohols by the hydroformylation of olefins. More particularly, this invention relates to a unique method for in-situ preparation of an activated carbonaceous preformer catalyst which is used to effect the conversion of cobalt salts to the active cobalt species in the cobalt catalyzed hydroformylation of the olefins.

BACKGROUND OF THE INVENTION

The oxo process is the commercial application of the hydroformylation reaction for making higher alcohols and aldehydes from olefins. In the cobalt oxo process, an olefin reacts with carbon monoxide and hydrogen (i.e., syn gas) at elevated temperatures in the presence of a cobalt carbonyl catalyst to produce a hydroformylation reaction product which is subsequently decobalted or demetalled to produce a crude product mixture of aldehydes, alcohols, acetals, formates, unreacted olefins and secondary products. Subsequent hydrogenation steps provide the desired finished alcohol products commonly referred to as oxo alcohols (i.e., alcohols produced by an oxonation reaction).

One aspect of the overall cobalt oxo process involves the preparation of the active cobalt catalyst species which is hydrido cobalt carbonyl ($HCo(CO)_4$). Commercial oxo processes employ a preforming step in which this active cobalt catalyst species is prepared from a cobalt salt, e.g., cobalt formate, using a noble metal preforming catalyst. This preforming step is disclosed, for example, in U.S. Pat. No. 4,404,119, which issued Sep. 13, 1983, to Lagace et al. and in U.S. Pat. No. 4,255,279, which issued Mar. 10, 1981, to Spohn et al.

The present inventors have developed an improvement in the process for preparing oxo alcohols by the cobalt catalyzed hydroformylation of $C_2$ to $C_{17}$ linear or branched monoolefins with subsequent hydrogenation of the hydroformylation reaction product which has been disclosed in co-pending U.S. patent application, Ser. No 08/122,859, filed on Sep. 16, 1993. In this co-pending application the aqueous solutions of cobalt salts have been converted to active hydrido cobalt carbonyl species in a preformer reactor, the preformer containing (i) preformer metal catalyst of Group IB or VIII of the Periodic Table or (ii) a preformer non-metallic catalyst selected from the group consisting of activated carbon, ion exchange resins, silica alumina and zeolites. The preformer catalyst was reactivated according to co-pending U.S. patent application, Ser. No. 08/122,859 by treating it at a temperature of about 120° C. to 170° C. and at a pressure of about 13.88 MPa (2,000 psig) to 31.10 MPa (4,500 psig) and preferably about 20.77 MPa (3,000 psig), with water or with a mixture of water and hydrogen or a mixture of water and syn gas for a period of about 2 to 50 hours, whereby the conversion of the cobalt salts to hydrido cobalt carbonyl is improved when such salts are contacted with the treated preformer catalyst.

The use of activated carbon as a preformer catalyst, as suggested in U.S. patent application, Ser. No. 08/122,859, fails to produce the catalytic activity necessary for converting the cobalt salt to hydrido cobalt carbonyl in sufficient yields when the organic employed in the preformer is a hydrocarbon, an alcohol containing eight or more carbon atoms, a hydroformylation product (i.e., aldehydes, paraffins and unconverted olefins) or a hydrogenation product (i.e., paraffins and unconverted olefins). It would be highly desirable to be able to use activated carbon or other carbonaceous materials as the preforming catalyst since this material is substantially less expensive than conventional preformer metal catalysts of Group IB or VIII of the Periodic Table, i.e., palladium.

The present inventors have developed a unique process which increases the catalytic activity of carbonaceous materials such that they can be successfully used as preforming catalysts in the conversion of cobalt salt to hydrido cobalt carbonyl in the presence of any organic stream.

The process of the present invention utilizes an aqueous cobalt salt solution in the presence of light alcohols and syn gas at elevated pressures and temperatures to activate the carbonaceous material by depositing cobalt, e.g., hydrido cobalt carbonyl, on the surface thereof. The deposited cobalt then acts as a preforming initiator which substantially increases the catalytic activity of the carbonaceous material.

The present inventors have discovered that using carbonaceous catalysts during preforming of cobalt salts in the presence of light alcohols promotes more rapid formation and deposition of hydrido cobalt carbonyl on the surface of the catalyst than when other types of organics are used. The use of light alcohols with the cobalt salts also prevents deposition of cobalt as cobalt metal or cobalt salts on the carbon surface.

On the other hand, treating carbonaceous preforming catalysts with an aqueous cobalt salt solution in the presence of other organics (e.g., heavy alcohols or aldehydes) or as a mixture of light alcohols and other organics as suggested in U.S. patent application, Ser. No. 08/122,859 will not produce catalytic activity equivalent to that of the present invention.

SUMMARY OF THE INVENTION

The present invention activates and/or regenerates carbonaceous preformer catalysts by treating them with an aqueous cobalt salt solution in the presence of a light alcohol (e.g., hexyl or heptyl alcohol) and syn gas at a temperature of about 120° C. to 190° C. and at a pressure of about 13.88 MPa (2,000 psig) to 31.11 MPa (4,500 psig) for a period of about 2 to 50 hours prior to passing any other organics over the catalysts, whereby the conversion of the cobalt salts to hydrido cobalt carbonyl in the presence of the activated carbonaceous catalyst is substantially improved compared to conversion in the presence of untreated carbonaceous catalysts.

The treatment of the carbonaceous catalyst with an aqueous cobalt salt solution in the presence of a light alcohol results in the formation and deposition of cobalt, e.g., hydrido cobalt carbonyl, on the surface of the carbonaceous preformer catalyst. The deposited hydrido cobalt carbonyl substantially increases the catalytic activity of the carbonaceous catalyst, i.e., reducing the induction period from over 60 minutes with fresh untreated carbon to about 20 minutes or less with treated or "seasoned" carbon.

The carbonaceous preformer catalyst is preferably activated carbon, although any carbonaceous material having a high surface area would also be suitable as a preformer catalyst.

The light alcohol comprises at least one light alcohol selected from alcohols containing from about 4 to 7 carbon atoms.

The other organic streams which may be processed over the carbonaceous preformer catalyst subsequent to treating the catalyst with light alcohol typically include one or more of the following: a hydrocarbon, a hydroformylation product, a hydrogenation product, or an alcohol containing 8 or more carbon atoms. These other organics may be used as required by process logistics, and would serve only to extract preformed cobalt from the water phase as it is formed. Any catalytic activity would result primarily from the "seasoned" or activated carbon as obtained from prior treatments with the mixture of light alcohol and aqueous cobalt salt.

DESCRIPTION OF THE PREFERRED EMBODIMENTS

Figure 1:
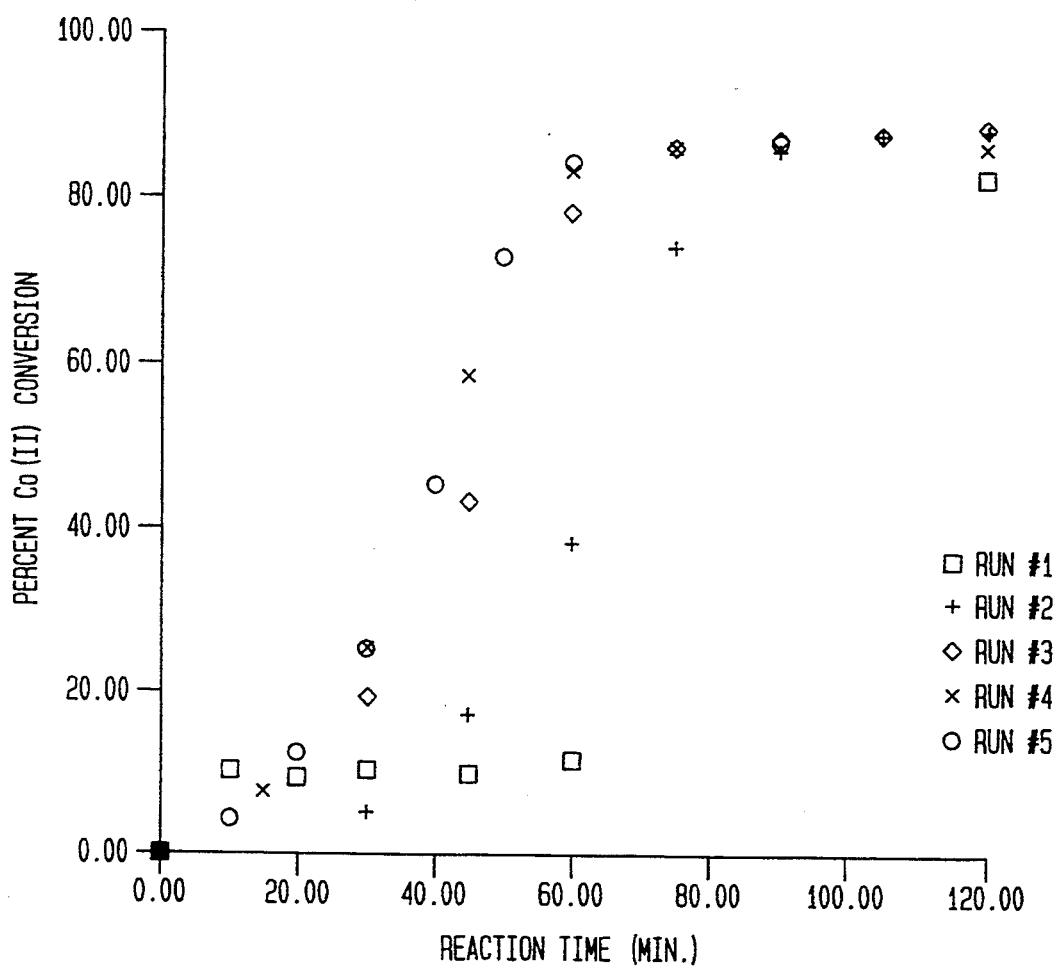
FIG. 1 is a graph plotting reaction time versus percent Co(II) conversions as carbon activation occurs during 5 batch autoclave experiments which used hexyl alcohol as the alcohol.

The present invention is typically employed in an oxo process in which the olefin is preferably a mixture of linear and branched $C_2$ to $C_{17}$ monoolefins, the hydroformylation typically being carried out at a pressure of 13 to 32 MPa and at a temperature of about 120° C. to 190° C. Cobalt is present as hydrido cobalt carbonyl in a concentration of from about 0.05 to 3.0 wt. %, calculated as metallic cobalt based on olefin feedstock. The synthesis gas (hydrogen and carbon monoxide) typically has a $H_2$:CO molar ratio in the range of 0.9:1 to 1.5:1, preferably about 1:1.

Particularly preferred carbonaceous preformer catalysts are extruded or granular activated carbons and any other carbonaceous material having a sufficiently high surface area.

In the operation of the oxo process the preformer treats an aqueous feed containing cobalt salt which is obtained from an acid/air demetalling step, or from the Cobalt Flash stripper bottom, followed by concentration in an evaporator or a flash unit. This operation is disclosed in U.S. Pat. No. 5,237,105, issued Aug. 17, 1993, to Summerlin.

Typically, as disclosed in the Summerlin patent, preforming is carried out in the presence of a cobalt free organic phase to provide continuous extraction of the product carbonyl from the aqueous phase into the organic phase. The cobalt free organic phase can be a hydrocarbon stream, an alcohol stream, a hydroformylation reaction product or a hydrogenation product. The continuous extraction effectively drives the reaction to higher levels of conversion and prevents deposition of cobalt as cobalt metal and salts on the catalyst surface.

The present inventors have discovered that by first co-processing the aqueous phase containing the cobalt salts over the carbon catalyst with a cobalt free light alcohol stream, carbon activation or seasoning takes place in addition to extraction of hydrido cobalt carbonyl. This activation or seasoning is the result of active cobalt species (i.e., hydrido cobalt carbonyl) depositing on the carbon surface thereby imparting catalytic activity for the autocatalytic preforming reaction. Subsequent preforming operation using the activated or seasoned carbon catalyst with other organic streams such as hydrocarbon streams, hydroformylation products or hydrogenation products result in improved performance relative to carbon catalysts that have not been seasoned or activated in such a manner.

The present invention is applicable for both the initial activation of the preformer catalyst or for the regeneration of a previously used preformer catalyst, thus, the term "activation" as used herein also applies to regeneration of used catalyst.

The activation procedure of this invention may be conducted over a temperature range of about 120° C. to 190° C., preferably at about 150° C. to 170°C., and a pressure of 13.88 MPa to 31.11 MPa (2,000 to 4,500 psig), preferably about 27.66 MPa (4,000 psig). The catalyst is advantageously treated with an aqueous cobalt salt solution in the presence of a light alcohol and syn gas prior to contacting the catalyst with any subsequent organic streams. The treatment should be conducted for a period of about 2 to 50 hours.

The light alcohol or activation solvent is preferably an alcohol containing 4 to 7 carbon atoms. The light alcohol is typically present in the preformer reactor in a volume ratio of between 0.5:1 to 5:1 light alcohol to aqueous cobalt salt solution.

During the activation with the light alcohol and aqueous cobalt salt solution, the syn gas is typically present in a concentration between about 8:1 to 28:1 moles of syn gas to moles of cobalt salt.

For fresh catalyst activation, the time of treatment is the time required to deposit hydrido cobalt carbonyl onto the surface of the catalyst, and for regeneration it is the time required to displace heavy organic material from the pores and replace with hydrido cobalt carbonyl.

EXAMPLE 1

An extruded activated carbon catalyst was charged to a batch autoclave reactor and contacted with an aqueous cobalt formate solution and hexyl alcohol in the presence of $H_2$ and CO at 4,000 psig (27.66 MPa) and 120° C. The hexyl alcohol:cobalt formate solution volume ratio and the $H_2$:CO molar ratio were both 1:1. The conversion of Co(II) as a function of reaction time was measured during a series of batch runs and the results are set forth in FIG. 1, attached hereto. The promoting ability of the activated carbon material is seen to increase as activation or "seasoning" occurs after several batch runs, as indicated by reducing the induction period from more than 60 minutes on the first run to 20 minutes or less on the fifth run using the same carbon.

EXAMPLE 2

Figure 2:
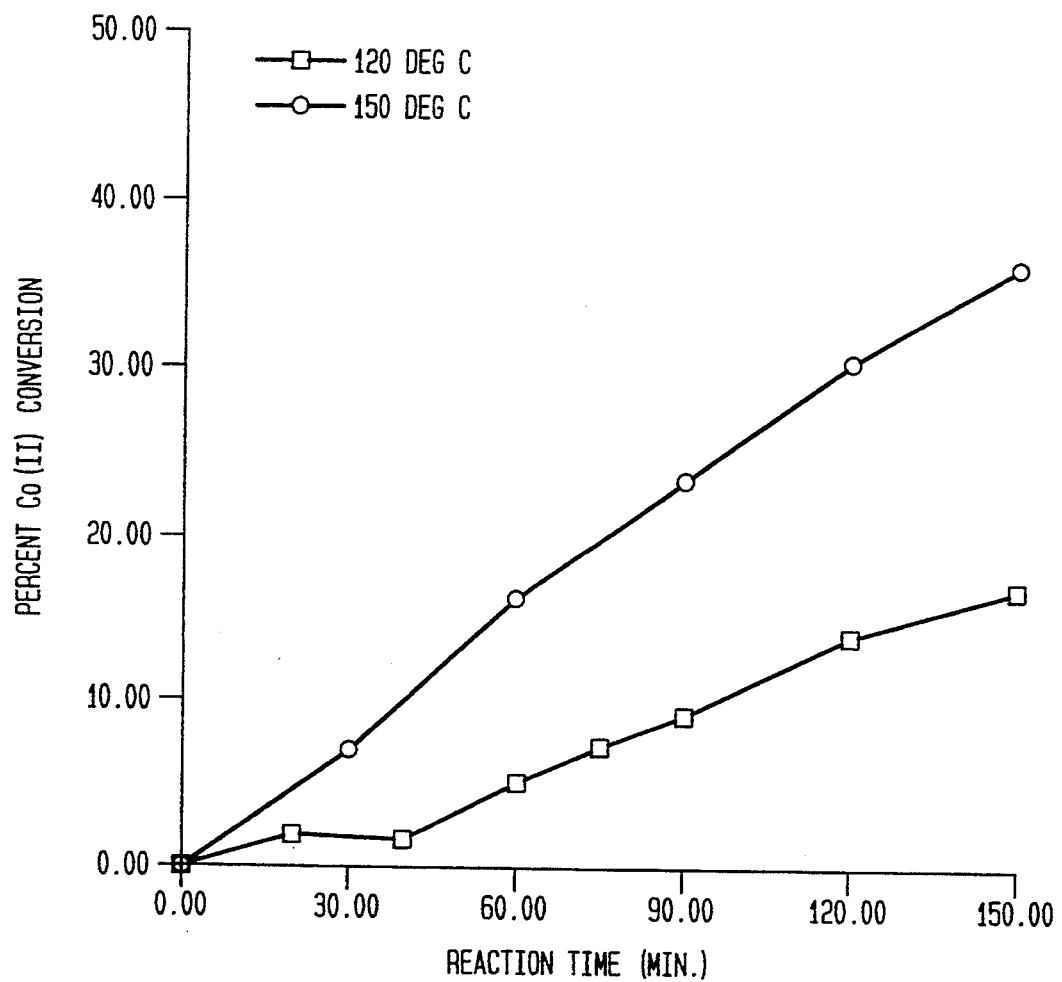
FIG. 2 is a graph plotting reaction times versus percent Co(II) conversions to demonstrate the ability of the "seasoned" or activated carbon to initiate cobalt carbonyl preforming at 120° C. and 150° C. when a hydrocarbon is used in place of the hexyl alcohol.

The activated carbon from Example 1 above was contacted with an aqueous cobalt formate solution and a hydrocarbon in the presence of $H_2$ and CO at 4,000 psig (27.66 MPa). The hydrocarbon:cobalt formate solution volume ratio and the $H_2$:CO molar ratio were both 1:1. Previous experience has shown that hydrocarbons are very poor preforming initiators, and any observed activity is due solely to the catalytic material which may be present. As shown in FIG. 2, attached hereto, the activated carbon was able to initiate the preforming reaction, and this effect was enhanced at higher temperatures.

EXAMPLE 3

Figure 3A:
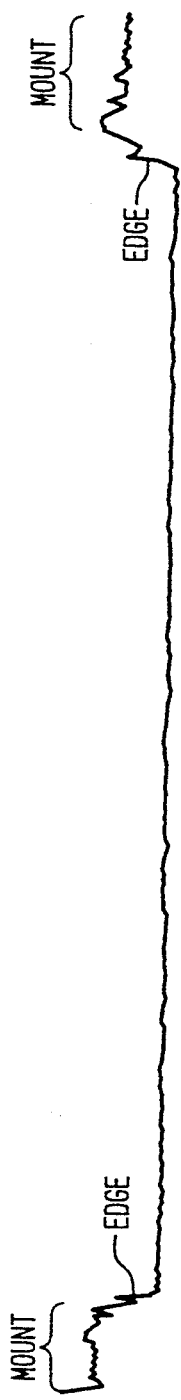
FIG. 3a is an electron probe analysis through a cross-section of an untreated carbon catalyst which illustrates the flat baseline obtained when no cobalt is present on the carbon.
Figure 3B:
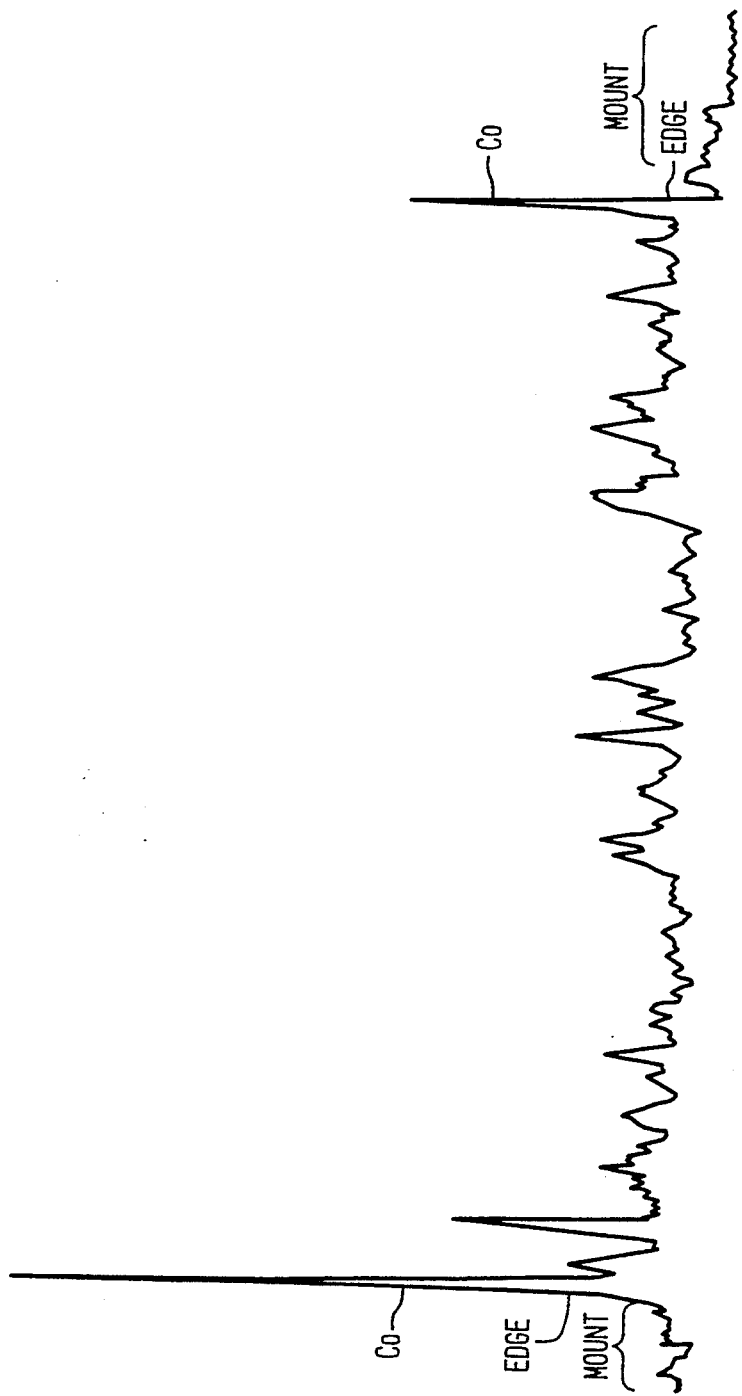
FIG. 3b is an electron probe analysis which shows cobalt deposition through a cross-section of a carbon catalyst after treatment with an aqueous cobalt salt solution in the presence of hexyl alcohol and syn gas.

FIGS. 3a and 3b depict the results of an electron probe analysis. FIG. 3a shows an electron probe analysis of an untreated activated carbon catalyst where no cobalt was detected through the cross-section of the extrudate, as indicated by the flat baseline. FIG. 3b, however, clearly shows substantial amounts of cobalt deposited at the edges and through the cross-section of an activated carbon catalyst treated with an aqueous cobalt salt solution in the presence of a light alcohol and syn gas. The deposition of cobalt on the activated carbon catalyst is indicative of increased catalytic activity observed during batch autoclave experiments described in Example 1. Therefore, the treated activated carbon catalyst has substantially greater catalytic activity than the untreated catalyst.

EXAMPLE 4

100 cc of carbon in the form of 2 mm diameter by 3 to 5 mm length extrudates was charged to a tubular reactor and tested for cobalt preforming activity which was measured as conversion of cobalt formate to hydridocobalt carbonyl.

Initial operating conditions were 3000 psig (20.77 MPa), 140° C., 150 Gas Hourly Space Velocity (GHSV) of 1:1 molar ratio $H_2$/CO synthesis gas and 2.5 Liquid Hourly Space Velocity (LHSV) of 1:1 volume ratio of $C_{10}$ LOF to aqueous cobalt formate solution. Gas hourly space velocity is defined as volume of gas at standard conditions per hour per volume of catalyst. Liquid hourly space velocity is defined as total volume of liquid feed per hour per volume of catalyst. $C_{10}$ LOF is the name given to the light oxo fraction from production of $C_{10}$ alcohol by carbonylation of $C_9$ olefin feed. It is a mixture of unconverted $C_9$ olefin feed and any $C_9$ paraffin formed in the oxo process. The aqueous cobalt formate solution contained 1 wt. % cobalt. After 18.5 hours of operation in this mode, the conversion of cobalt formate in the aqueous cobalt formate solution was measured to be 17.5%. A second measure of cobalt formate conversion taken after 53.5 hours of operation indicated 18% conversion. For the purpose of this test, this level of conversion is defined as the level obtained on carbon that is not pretreated or activated by initially operating with hexyl alcohol as the organic.

At this point in the experiment, the organic stream was changed from $C_{10}$ LOF to hexyl alcohol and the liquid feed rate was increased to 5 LHSV. All other process conditions remained the same. The purpose of switching from $C_{10}$ LOF to hexyl alcohol was to activate the carbon support material for converting cobalt formate to hydridocobalt carbonyl. To illustrate the activating effect of operating with hexyl alcohol as the organic, conversion of cobalt formate was measured at frequent intervals and the results shown below in Table 1:

TABLE 1

| Total Time on Feed (hours) | Time of Operation with Hexyl Alcohol (hours) | Cobalt Formate Conversion (%) |
|---|---|---|
| 54.5 | 1.0 | 18.9 |
| 55.0 | 1.5 | 23.8 |
| 55.5 | 2.0 | 25.8 |
| 56.0 | 2.5 | 26.7 |
| 82.5 | 29.0 | 33.7 |
| 102.0 | 48.5 | 28.8 |
| 154.0 | 100.5 | 28.5 |

At this point in the experiment, the organic stream was returned to $C_{10}$ LOF from hexyl alcohol. Operating conditions were as described during the earlier part of the experiment with $C_{10}$ LOF as the organic. At 199 total hours on feed, the conversion of cobalt formate was measured to be 23.8% which is greater than the 18% conversion of cobalt formate obtained prior to activation of the carbon from operation with hexyl alcohol as organic, illustrating the ability to operate at increased activity using other organics after an activation treatment with hexyl alcohol as organic.

Figure 4:
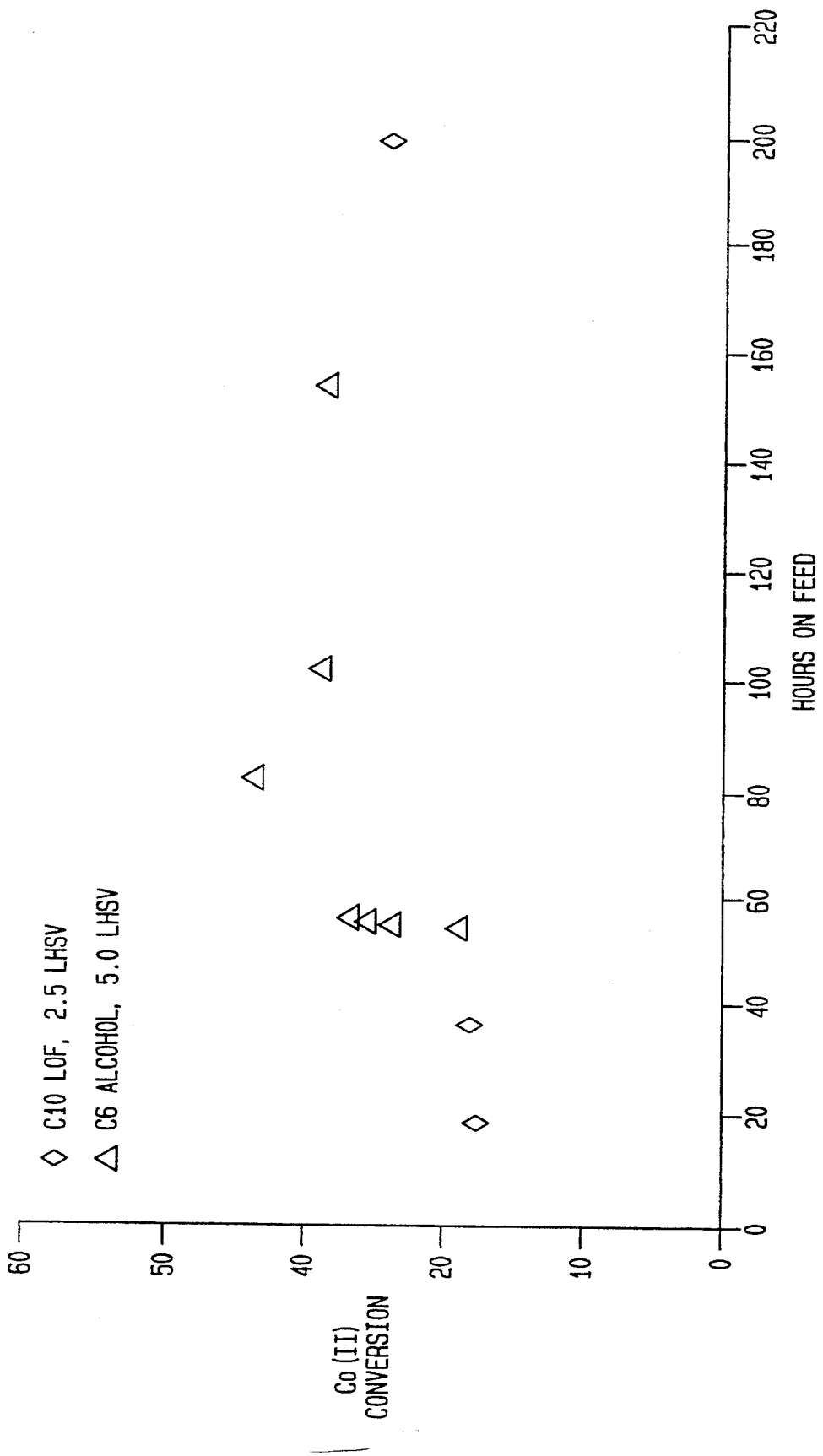
FIG. 4 is a graph plotting Co(II) conversion for a feed of hydrocarbon/cobalt salt, followed by treatment with a feed of hexyl alcohol/cobalt salt, and then returned to a feed of hydrocarbon/cobalt salt.

FIG. 4 illustrates these experimental results as a graph of the percent Co(II) conversion.

What is claimed is:

1. A process for preparing oxo alcohols and aldehydes by the cobalt catalyzed hydroformylation of $C_2$ to $C_{17}$ linear or branched monoolefins with subsequent hydrogenation of the hydroformylation product, in which oxo process aqueous solutions of cobalt salts are converted to active hydrido cobalt carbonyl species in a preformer reactor, said preformer reactor containing a carbonaceous preformer catalyst, the improvement which comprises activating said carbonaceous preformer catalyst by treating it at a temperature of about 120° C. to 190° C. and a pressure of about 13 MPa to 32 MPa with an aqueous cobalt salt solution in the presence of light alcohol and syn gas for about 2 to 50 hours, whereby the conversion of said cobalt salts to said active cobalt catalyst species is improved when said salts are contacted with the treated carbonaceous preformer catalyst.

2. The process according to claim 1 wherein said carbonaceous preformer catalyst is activated carbon.

3. The process according to claim 1 wherein said light alcohol stream comprises at least one light alcohol selected from the group consisting of: alcohols containing from about 4 to 7 carbon atoms.

4. The process according to claim 1 wherein said activation temperature is in the range between about 150° C. to 170° C.

5. The process according to claim 1 wherein the induction period for conversion of said cobalt salts to said active cobalt catalyst species in the presence of said treated carbonaceous preformer catalyst is about 20 minutes or less.

6. The process according to claim 1 wherein hydrido cobalt carbonyls are deposited on the surface of said carbonaceous preformer catalyst upon treatment with said aqueous cobalt salt solution in the presence of said light alcohol and syn gas.

7. The process according to claim 1 wherein said preformer catalyst is treated with said aqueous cobalt salt solution in the presence of said light alcohol and syn gas prior to contacting with any other organic stream, said other organic stream comprises at least one compound selected from the group consisting of: alcohols containing 8 or more carbon atoms, hydrocarbons, hydroformylation products, and hydrogenation products.

8. The process according to claim 1 wherein said light alcohol is present in said preformer reactor in a volume ratio of between 0.5:1 to 5:1 light alcohol to aqueous cobalt salt solution.

9. The process according to claim 1 wherein said syn gas in a molar ratio of $H_2:CO$ of about 0.5:1 to 1.5:1 is present in said preformer reactor in a concentration between about 8:1 to 28:1 moles of syn gas to moles of cobalt salt.

* * * * *